US005776772A

United States Patent [19]

Paulson et al.

[11] Patent Number: 5,776,772
[45] Date of Patent: *Jul. 7, 1998

[54] METHOD FOR PRODUCING SECRETABLE GLYCOSYLTRANSFERASES AND OTHER GOLGI PROCESSING ENZYMES

[75] Inventors: James G. Paulson, Del Mar; Eryn Ujita-Lee, Redondo Beach, both of Calif.; Karen J. Colley, Oak Park, Ill.; Beverly Adler, Newbury Park, Calif.; Jeffrey K. Browne, Camaville, Calif.; Jasminder Weinstein, Westlake Village, Calif.

[73] Assignee: The Regents of the University of California, Oakland, Calif.

[*] Notice: The term of this patent shall not extend beyond the expiration date of Pat. Nos. 5,032,519 and 5,541,083.

[21] Appl. No.: 593,865

[22] Filed: Jan. 30, 1996

Related U.S. Application Data

[62] Division of Ser. No. 209,604, Mar. 10, 1994, Pat. No. 5,541,083, which is a continuation of Ser. No. 849,045, filed as PCT/US90/06088 Oct. 24, 1990, abandoned, which is a continuation-in-part of Ser. No. 426,577, Oct. 24, 1989, Pat. No. 5,032,517.

[51] Int. Cl.[6] .................. C12N 15/63; C12N 15/00; C12N 15/54; C12N 15/79
[52] U.S. Cl. .................. 435/320.1; 435/41; 435/69.1; 435/70.1; 435/172.3; 435/97; 435/197; 435/100; 435/325; 935/48; 935/60; 935/70; 935/72; 935/47; 536/23.5

[58] Field of Search .................. 435/320.1, 41, 435/69.1, 70.1, 172.3, 97, 197, 100, 240.2, 325; 935/48, 60, 70, 72, 47; 536/23.5

[56] References Cited

U.S. PATENT DOCUMENTS

| 5,032,519 | 7/1991 | Paulson et al. | 435/193 |
| 5,541,083 | 7/1996 | Paulson et al. | 435/41 |

OTHER PUBLICATIONS

Gil et al Cell 41:249–258, 1985.

Smith et al J. Biol. Chem 252: 7294–7299, 1977.

Weinstein et al. J. Biol. Chem. 262: 17735–17743, 1987.

*Primary Examiner*—Brian R. Stanton
*Assistant Examiner*—Jill D. Schmuck
*Attorney, Agent, or Firm*—Oppenheimer Poms Smith

[57] ABSTRACT

A method for genetically engineering cells to produce soluble and secretable Golgi processing enzymes instead of naturally occurring membrane-bound enzymes. Cells are genetically engineered to express glycosyltransferases which lack both a membrane anchor and a retention signal. The resulting altered enzyme becomes soluble and secretable by the cell without losing its catalytic activity. Secretion of the soluble glycosyltransferase by the cell provides for increased production and simplified recovery of glycosyltransferase.

5 Claims, 6 Drawing Sheets

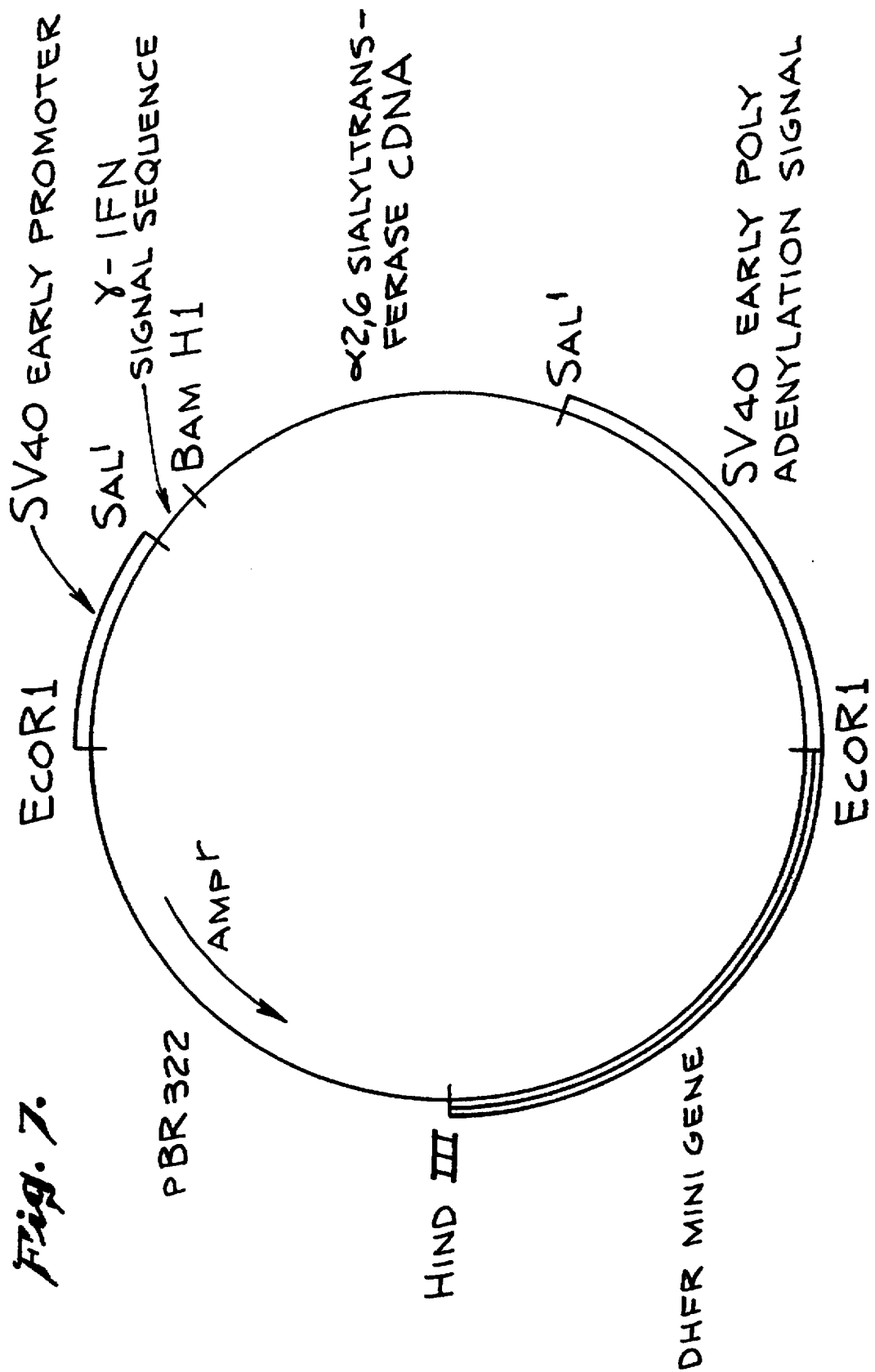

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:

( A ) LENGTH: 4 amino acids ( B ) TYPE: amino acid ( D ) TOPOLOGY: linear ( i i ) MOLECULE TYPE: protein ( x i ) SEQUENCE DESCRIPTION: SEQ ID NO:1:

Lys Asp Glu Leu

METHOD FOR PRODUCING SECRETABLE GLYCOSYLTRANSFERASES AND OTHER GOLGI PROCESSING ENZYMES

This is a divisional of application Ser. No. 08/209,604, filed on Mar. 10, 1994, now U.S. Pat. No. 5,541,083, which is a continuation of Ser. No. 07/849,045, filed on May 27, 1992, now abandoned, which is the United States National phase of PCT application Serial number US90/06088 filed Oct. 24, 1990 which is a continuation-in-part of Ser. No. 07/426,577, filed Oct. 24, 1989, now U.S. Pat. No. 5,032,517.

BACKGROUND OF THE INVENTION

1. Field of the Invention

The present invention relates generally to the cellular mechanisms and enzymes involved in the glycosylation of proteins manufactured by the cell. More particularly, the present invention involves altering the enzyme production capabilities of a cell in order to produce a soluble glycosyltransferase which is secreted by the cell and recovered for further use.

2. Description of Related Art

This invention was made with government support under Grant Contract Nos. GM-27904 and GM-1157 awarded by the National Institute of Health. The government has certain rights in this invention. The publications and other reference materials referred to herein to describe the background of the invention and to provide additional detail regarding its practice are hereby incorporated by reference. For convenience, the reference materials are numerically referenced and grouped in the appended bibliography.

Glycosyltransferases are important enzymes which are essential to the cellular synthesis of carbohydrates. The glycosyltransferases and their role in enzyme-catalyzed synthesis of carbohydrates are presently being extensively studied (43,44). These enzymes exhibit high specificity for forming carbohydrate structures of defined sequence. Consequently, purified glycosyltransferases are increasingly used as enzymatic catalysts in carbohydrate synthesis. Application of these enzymes has been limited because of difficulties in isolating and purifying them. As a result, glycosyltransferases are only available in very small amounts and are extremely expensive.

The isolation and purification of glycosyltransferases is difficult because of their low abundance in cells and because the enzymes are membrane-bound glycoproteins which reside in the Golgi apparatus of cells. Accordingly, the presently utilized purification procedures involve the use of animal tissues from which the enzymes must be extracted and purified. The standard purification techniques, moreover, typically produce preparations which contain a small but significant percentage of the isolated enzymes which remain membrane bound. Thus, these purification procedures are not amenable to large scale production and therefore are not well suited to meet the present and future demands for purified enzymes to be used in research and in industrial applications involving synthesis of carbohydrates.

As a result, there is presently a need to provide methods for producing increased amounts of purified soluble glycosyltransferases, uncontaminated by membrane bound glycosyltransferases, wherein the method is amenable to relatively large scale production of purified enzymes.

SUMMARY OF THE INVENTION

In accordance with the present invention, a method is disclosed for producing catalytically active glycosyltransferases which are soluble and therefore readily secreted from cells. The secretion of relatively large quantities of such catalytically active enzymes provides a simplified procedure for purifying and recovering the glycosyltransferases. The invention is based upon the discovery that glycosyltransferases may be converted from membrane-bound proteins to soluble proteins without destroying their enzymatic character.

The present invention involves genetically altering a cell so that it produces a soluble glycosyltransferase instead of the normal membrane-bound glycosyltransferase. It was discovered that cells can be genetically altered to produce soluble glycosyltransferases which are readily secreted by the cell. The secreted glycosyltransferases are then readily recovered by conventional procedures for use in industrial applications and research involving carbohydrate synthesis.

As a feature of the present invention, it was discovered that the membrane domain and the stem portion of glycosyltransferases functioned, respectively, as the membrane anchor and retention signal to keep the enzyme bound to the Golgi membrane. Further, it was discovered that the enzymatic activity of glycosyltransferases is not dependent on the stem portion so that it can be substantially removed or replaced without destroying the catalytic activity of the glycosyltransferase. In accordance with the present invention, genes are introduced into the cell which express glycosyltransferases that have the membrane anchor and stem portion substantially removed and replaced with a cleavable secretion-signal peptide. As a result, the glycosyltransferase becomes soluble and is secreted by the cell.

The homogeneous, soluble glycoslytransferases of the present invention are generally substantially less contaminated by membrane-bound glycosyltransferases than those produced by standard methods. The soluble glycosyltransferases are suitable for a variety of uses, such as enzymatically synthesizing oligosaccharides on a large scale by, for example, serially reacting a starting oligosaccharide with a succession of soluble glycosyltransferases and the appropriate sugar nucleotides.

The above discussed and many other features and attendant advantages of the present invention will become better understood by reference to the following detailed description when taken in conjunction with the accompanying drawings.

BRIEF DESCRIPTION OF THE DRAWINGS

FIG. 7 is a diagram showing the exemplary vector construction used to transfect CHO with the gene expressing the soluble sp-ST protein.

DETAILED DESCRIPTION OF THE INVENTION

Figure 1:
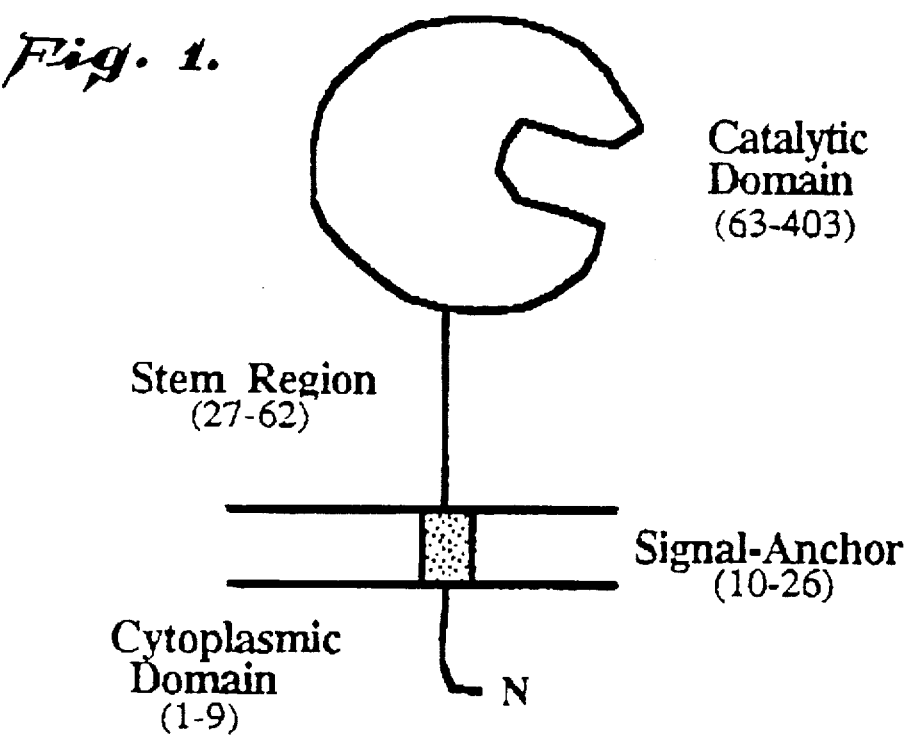
FIG. 1 shows the domain structure of the sialyltransferase which is anchored to Golgi apparatus membranes by an $NH_2$-terminal hydrophobic domain. The stem region is believed to carry the retention signal that keeps the enzyme in the Golgi apparatus.

The present invention involves controlling the production of glycosyltransferases in a cell by using genetic engineering to instruct the cell to produce glycosyltransferases which are soluble and can be secreted by the cell. This is accomplished by instructing the cell to produce glycosyltransferases which are lacking both a membrane anchor domain and a retention signal which are believed to normally anchor the glycosyltransferase in the Golgi apparatus of the cell. The cell is instructed to secrete the glycosyltransferase, as opposed to producing it intracellularly, by incorporating in the genetic material and instructions for producing a cleavable secretion-signal peptide. It was discovered that the membrane anchor and retention signal can be removed from glycosyltransferases without destroying the catalytic activity of the enzyme. The resulting soluble peptide is sorted by the cell and transported out of the cell for recovery and further use.

A major consideration in cell biology is sorting and transport of glycosyltransferases and other membrane glycoproteins to their multiple destinations. One hypothesis is that glycoproteins destined for the cell surface are transported by a default pathway and require no routing information, while glycoproteins destined for other subcellular localizations require signals that assist in their sorting and transport (1–3). One well documented transport signal is the mannose 6-phosphate recognition marker found on some lysosomal enzymes (4). These transport signals mediate the enzymes' recognition by mannose 6-phosphate receptors which transport them to the lysosomes as they exit the biosynthetic pathway from the trans-Golgi. In the case of resident proteins of the ER and the Golgi apparatus, the putative signals are viewed as retention signals, since the transport mechanism is likely the same as the default pathway, and the proteins must then resist the flow of the default pathway once they arrive at their site of residence (1–3).

Progress has been made in elucidating the retention signals for the endoplasmic reticulum (ER) retained proteins (6–10). Analysis of deletion mutants and fusion proteins of soluble ER proteins such as protein disulfide isomerase, prolyl hydroxylase, grp78, and grp94 has demonstrated that a COOH-terminal Lys-Asp-Glu-Leu (SEQ ID NO.1) sequence is sufficient for retention in the ER (6,7). In this case a resident Lys-Asp-Glu-Leu (SEQ ID NO.1) receptor protein is postulated for retention of these proteins, although such a receptor has not been identified. Less is known about the retention signals of membrane-bound proteins of the ER (8–10).

Elucidation of the signals for retention of membrane proteins in the Golgi apparatus has been equally refractory. Machamer and Rose (11) have demonstrated that the first of three membrane-spanning regions of the E1 protein of coronavirus is required for the localization/retention of this viral protein to the cis- to medial-Golgi complex. How this region participates in Golgi apparatus localization is not yet understood.

β-galactoside α2,6-sialyltransferase is a membrane bound glycosyltransferase of the Golgi apparatus which participates in the addition of terminal sialic acid residues to N-linked oligosaccharide chains. Studies have been conducted to identify the structural basis for localization of this enzyme within the cell (14,15). In rat liver hepatocytes, hepatoma cells, and in intestinal globlet cells, β-galactoside α2,6-sialyltransferase has been localized by immunoelectron microscopy to the transcisternae of the Golgi and the trans-Golgi network, whereas in intestinal absorptive cells, the enzyme is more diffusely localized throughout the cisternal stacks (14–16).

As diagrammed in FIG. 1, the rat liver sialyltransferase is believed to be a class 11 membrane glycoprotein protein with a 9-amino acid $NH_2$-terminal cytoplasmic tail, a 17-amino acid signal-anchor domain, and a luminal domain which includes an exposed stem region followed by a 41-kDa catalytic domain (19). The existence of an exposed stem region was initially suggested by the purification of a soluble form of the rat liver sialyltransferase which was missing the first 62 amino acids due to proteolytic degradation during isolation. Soluble forms of the sialyltransferase also are found in various secretions and body fluids including milk and colostrum (18) and serum (20,21). The slow release of the sialyltransferase catalytic domain from the transmembrane anchor, through the action of endogenous proteases in the Golgi apparatus or trans-Golgi network, has been proposed to account for the appearance of the soluble enzyme in these fluids (21,22).

The above considerations suggest that sialyltransferase may act like any other secretory protein once released from its $NH_2$-terminal signal-anchor, providing that the signal for retention in the Golgi apparatus is not part of the catalytic domain of the enzyme. As set forth in more detail below, the present invention is based on the discovery that the $NH_2$-terminal signal-anchor and stem region of the sialyltransferase can be replaced with a cleavable signal sequence to produce a secretable enzyme which retains its catalytic activity. Proteins transported across the cell membrane typically have an N-terminal sequence rich in hydrophobic amino acids about 15 to 30 amino acids long. Sometime during the process of passing through the membrane, the signal sequence is cleaved by signal peptidase. Watson et al., *Molecular Biology of the Gene* (The Benjamin/Cummings Publishing Co., Inc., Menlo Park, Calif. 1987), which is incorporated herein by reference. Many sources of signal peptides are well known to those skilled in the art and can include, for example, the insulin signal sequence, the tissue plasminogen activator signal sequence, and the like. In general, the N-terminus of essentially any secreted protein is a potential source of a signal sequence suitable for use in the present invention.

In accordance with the present invention, it was found that removal of the sialyltransferase membrane-anchor alone is not sufficient for rapid and efficient secretion of the soluble glycosyltransferase. Construction and expression of a sialyltransferase mutant in which the anchor sequence is replaced by a cleavable signal peptide by recombinant DNA techniques results in a soluble sialyltransferase missing the N-terminal 28 amino acids but containing the intact stem region. This mutant is localized to the Golgi apparatus prior to being slowly secreted from the cell ($t_{1/2} \geq 24$ hours). In contrast, the soluble sialyltransferase construct missing the N-terminal 57 amino acids is rapidly secreted from the cell ($t_{1/2}$ 2–3 hours). These results show that a retention signal for Golgi apparatus localization resides in the stem region of the sialyltransferase and, in accordance with the present invention, if substantially all of the stem region as well as the signal-anchor domain of the sialyltransferase is removed, rapid and efficient secretion of the soluble glycosyltransferase will be obtained. Preferably, fewer than about ten stem region amino acids remain on the secreted enzyme, more preferably about three, or less.

The number of stem region amino acids that must be removed to eliminate a functional retention signal can be readily determined by, for example, producing different recombinant constructs which have various deletions or modifications of the gene and observing the rate of secretion by a transformed cell. The precise number of stem region amino acids remaining is not critical so long as a functional retention signal is eliminated. A secretable, soluble glycosyltransferase will most preferably have a $t_{1/2}$ of less than about 12 hours, and ideally between about 2 and about 3 hours. The term "$t_{1/2}$" as used herein is defined as the time required for half of the expressed soluble glycosyltransferase to be secreted from the transformed cell.

The present invention basically involves transfecting a host cell with a vector carrying a gene which expresses a glycosyltransferase that has the membrane anchor and most of the stem region replaced with a cleavable secretion signal segment. The resulting soluble glycosyltransferase, when expressed in the cell, is secreted by the cell. The secreted soluble glycosyltransferase is then separated from the cell media for use in industrial applications or carbohydrate synthesis research. Accordingly, the invention provides a useful procedure for producing relatively large amounts of easily recoverable homogeneous, soluble glycosyltransferases which retain their catalytic activity. The term "homogeneous, soluble glycosyltransferase" refers to a soluble glycosyltransferase composition which contains soluble glycosyltransferases substantially free of naturally associated proteins, including membrane bound glycosyltransferases, and/or agents, such as detergents, used to solubilize the enzyme. The term "substantially pure form" indicates at least 90% purity, preferrably 95–99% or more.

The invention has wide application to the production of glycosyltransferases including N-acetylglucosaminaltransferases, N-acetylgalactosaminyltransferases, sialyltransferases, fucosyltransferases, galactosyltransferases and mannosyltransferases providing that they exhibit similar topology to the sialyltransferase. Indeed, as summarized in FIG. 2 and Table 1, other glycosyltransferase cDNAs cloned to date also exhibit an $NH_2$-terminal signal-anchor sequence like the sialyltransferase, predicting the same topology found for the sialyltransferase (FIG. 1). The cloning, sequencing and domain structure of glycosyltransferases is known. See, e.g., Creeger, et al., *Methods Enzymol.*, 83:326 (1982); Creeger et al., *J. Biol. Chem.*, 254:804 (1979); Weinstein et al., *J. Biol. Chem.*, 262:17735 (1987); Paulson et al., *Biochem. Soc. Trans.*, 15:618 (1987); Ernst et al., *J. Biol. Chem.*, 264:3436 (1989); and Rajan et al., *J. Biol. Chem.*, 264: (1989); Larsen et al., *Proc. National Acad. Sci. USA*, 86:8227–8231 (1989); Larsen et al., *Proceedings National Academy of Science U.S.A.* 86:8227–8231 (1990); and Kukowska - Latallo et al., Genes and Development (1990), all of which are incorporated herein by reference. Other classes of Golgi apparatus enzymes involved in post-translational modifications may also exhibit similar topology, such as sulfotransferases, glycosidases, acetyltransferases, mannosidases, and could also be produced by this method. The following description will be limited to the production of a soluble sialyltransferase with it being recognized by those skilled in the art that other glycosyltransferases and Golgi processing enzymes having similar membrane attachment structures can also be produced in secretable forms in accordance with the present invention.

TABLE 1

| Glycosyltransferase | Donor Substrate | Sequence Formed |
|---|---|---|
| Galactosyltransferases | | |
| GlcNAcβ1, 4-GT (E.C.2.4.1.38) | UDP-Gal | Galβ1, 4GlcNAc-R |
| Gal α1, 3-GT (E.C.2.4.1.151) | UDP-Gal | Galα1, 3Galβ1, 4GlcNAc-R |
| Sialyltransferase | | |
| Gal α2,6-ST (E.C.2.4.99.1) | CMP-NeuAc | NeuAcα2, 6Galβ1, 4GlcNAc-R |
| Fucosyltransferases | | |
| GlcNAc α1,3-FT (E.C.2.4.1.65) | GDP-Fuc | Fucα1, 3 GlcNAc-R Galβ1, 4 Fucα1, 4 GlcNAc-R Galβ1, 3 |
| Gal α1,2-FT (E.C.2.4.1.69) | GDP-Fuc | Fucα1, 2Galβ1, 4GlcNAc-R |
| N-Acetylgalactosaminyltransferase | | Fucα1, 2Galβ1, 3GalcNAc-R |
| Gal α1,3-GalNAcT (Blood group A transferase) | UDP-GalNAc | GalNAα1, 3 Gal-R Fucα1, 2 |

The present invention relates to the use of recombinant DNA techniques to produce the claimed glycosyltransferases. Applicants believe that all of the techniques (e.g. isolation of nulceic acids, cloning, tranfection, and the like) are standard and well known in the art. The techniques used here generally follow those in Sambrook et al., *Molecular Cloning: A Laboratory Manual*, (Spring Harbor Laboratory Press, 2nd Ed. 1989), which is incorporated herein by reference.

Generally, to obtain sufficient amounts of a desired glycosyltransferase for large-scale reactions, the enzyme is cloned and expressed as a recombinant soluble enzyme according to the methods described more fully below. Suitable methods include isolation of RNA from a cell known to express the desired enzyme, followed by preparation of a cDNA library as described in Sambrook et al., supra. The desired cDNA is conveniently identified by subtraction using the method of Davis (Handbook of Experimental Immunology, Vol. 2, pgs. 1–13 (1986), which is incorporated herein by reference). The cDNA library is also suitable for probing with, for example, a nondegenerative probe to identify the desired clone. Alternatively, the cDNA library constructed in an expression vector is suitable for probing with an antibody to the desired enzyme. Standard transfection methods are used to produce mammalian or insect cell lines which express large quantities of the desired soluble glycosyltransferase which is then purified using standard techniques. See, e.g., Colley et al., *J. Biol. Chem.* 264:17619–17622 (1989) and *Guide to Protein Purification*, Vol. 182, Methods in Enzymology (Deutscher ed., 1990), both of which are incorporated herein by reference.

The host cell which is transfected can be any of the well known cell lines which are capable of producing glycosyltransferases. Exemplary cell lines include Chinese hamster ovary (CHO) cells, mouse L cells, mouse A9 cells, baby hamster kidney cells, C127 cells, PC8 cells, insect cells, yeast (saccharomyces cerevisae) and other eukaryotic cell lines capable of the expression of glycosyltransferases. The particular procedure used to introduce the altered genetic material into the host cell for expression of the soluble glycosyltransferase is not particularly critical. Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, CDNA, synthetic DNA or other foreign genetic material into a host cell (see Sambrook et al., supra). It is only necessary that the particular genetic engineering procedure utilized be capable of successfully introducing at least one gene into the host cell which is capable of expressing the altered glycosyltransferases.

The particular vector used to transport the genetic information into the cell is also not particularly critical. Any of the conventional vectors used for expression of recombinant glycoproteins in eukaryotic cells may be used. Expression vectors containing regulatory elements from eukaryotic viruses are typically used. SV40 vectors include pSVT7 and pMT2. Vectors derived from bovine papaloma virus include pBV-1MTHA, and vectors derived from Epstein Bar virus include pHEBO, and p205. Other exemplary vectors include pMSG, pAV009/A+, pMTO10/A+, pMAMneo-5, bacculovirus pDSVE, and any other vector allowing expression of glycoproteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells. For high expression of glycosyltransferases it is desirable to use a vector containing a DHFR gene such as pAV009/A+, pMTO10/A+ or the exemplary vector pDSVE described in detail below. Such vectors used in combination with CHO cells which are lacking DHFR (e.g., CHO DHFR) allow amplification of the vector DNA carrying the glycosyltransferase gene by selection of the cells with methotrexate. However, other selectable markers resulting in gene amplification such as the sodium, potassium ATPase gene and ouabain selection (45) would be equally suitable. Alternatively, high yield expression systems not involving gene amplification would also be suitable, such as using a bacculovirus vector in insect cells, with the glycosyltransferase under the direction of the polyhedrin promoter (46).

The expression vector of the present invention will typically contain both prokaryotic sequences that facilitate the propagation of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is frequently constructed from elements derived from different, well characterized viral or mammalian genes. For a general discussion of the expression of cloned genes in cultured mammalian cells, see Sambrook et al., supra, Ch. 16.

The prokaryotic elements that are typically included in the mammalian expression vector include a replicon that functions in *E. coli*, a gene encoding antibiotic resistance to permit selection of bacteria that harbor that recombinant plasmids, and unique restriction sites in nonessential regions of the plasmid to allow insertion of eukaryotic sequences. The particular antibiotic resistance gene chosen is not critical, any of the many resistance genes known in the art is suitable. The prokaryotic sequences are preferably chosen such that they do not interfere with the replication of the DNA in eukaryotic cells.

The expression vector contains a eukaryotic expression cassette that contains all the elements required for the expression of the glycosyltransferase DNA in eukaryotic cells. A typical expression cassette contains a promoter operably linked to the DNA sequence encoding a soluble glycosyltransferase and signals required for efficient polyadenylation of the transcript. The term "operably linked" as used herein refers to linkage of a promoter upstream from a DNA sequence such that the promoter mediates transcription of the DNA sequence. The DNA sequence encoding the glycosyltransferase will typically be linked to a cleavable signal peptide sequence to promote secretion of the encoded protein by the transformed cell. Additional elements of the cassette may include enhancers and, if genomic DNA is used as the structural gene, introns with functional splice donor and acceptor sites.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression*, (Cold Spring Harbor Pres, N.Y. 1983), which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes. If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucelotides, AAUAAA, located 11-30 nucelotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell. Genes encoding selectable markers are also typically used. Suitable selectable markers include, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, DHFR, and asparagine synthetase.

The present invention also relates to the use of recombinantly produced glycosyltransferases to produce specific oligosaccharides. The term "oligosaccharide" refers to a compound sugar or sugar moiety that yields two to ten monosaccharides upon hydrolysis. A "monosaccharide" is a single sugar unit that cannot be hydrolyzed into smaller units, it is typically a pentose, a hexose, or larger molecule. The starting oligosaccharide may be an oligosaccharide moiety on a glycoconjugate, such as a glycoprotein or a glycolipid or an unconjugated oligosaccharide. It may also be attached to a carrier moiety or to an activatable intermediate that will allow attachment to suitable carrier moiety. The starting oligosaccharide of the present invention typically comprises up to ten monosaccharides but may also be a single monosaccharide to which monosaccharides are added in succession by the appropriate glycosyltransferase to produce the desired oligosaccharide. The oligosaccharides are preferably prepared on a large scale so that economically efficient synthesis of a variety of oligosaccharides is feasible. For a general discussion of enzyme-catalyzed synthesis of oligosaccharides, see Toone et al., *Tetrahedron* 45: 5365–5422 (1989), and Sabesan et al., *J. Am. Chem. Soc.*, 108: 2068–2280 (1986), both of which are incorporated herein by reference.

Typically, the desired oligosaccharide is synthesized by sequentially reacting a starting oligosaccharide with a series of soluble glycosyltransferases of the present invention. Each enzymatic reaction for each glycosyltransferase uses the appropriate nucleotide sugar as a donor substrate. As used herein, the term "nucleotide sugar" refers to the activated form of sugars which are transferred to the oligosaccharide. These molecules are nucleoside phosphate sugars, such as UDP-Glc, UDP-GLcUA, UDP-GLCNAc, UDP-Gal, UDP-GalNAc, GDP-Man, GDP-Fuc, and CMP-NeuAc, and the like. The glycosyl transfer reactions are preferably carried out with added alkaline phosphotase (such as that from calf intestine, CIAP) in order to consume the nucleoside phosphate byproduct which may inhibit the reaction.

The nomenclature used to describe the oligosaccharides produced by the methods of the present invention follows the conventional nomenclature. Standard abbreviations for individual monosaccharides are used. For instance, 2-N-acetylglucosamine is represented by GlcNAc, 5-N-acetylneuraminic acid (a sialic acid) is NeuAc, fucose is Fuc, galactose is Gal, and glucose is Glc. Unless otherwise indicated, all sugars are D-isomers in the cyclic configuration. The two anomers of the cyclic forms are represented by a and B.

The monosaccharides are generally linked by glycosidic bonds to form oligo- and polysaccharides. The orientation of the bond with respect to the plane of the rings is indicated by $\alpha$ and $\beta$. The particular carbon atoms that form the bond between the two monosaccharides are also noted. Thus, a $\beta$glycosidic bond between C-1 of galactose and C-4 of glucose is represented by Gal$\beta$1,4Glc. For the D-sugars (e.g. D-GlcNAc, D-Gal, and D-NeuAc) the designation a means the hydroxyl attached to C-1 (C-2 in NeuAc) is below the plane of the ring and $\beta$ is above the ring. In the case of L-fucose, the $\alpha$ designation means the hydroxyl is above the ring and $\beta$ means it is below.

The following examples of the present invention describe the transfection of CHO cells with genes capable of expressing $\beta$-galactoside $\alpha$2,6-sialyltransferase (ST) in a modified form wherein the membrane anchor and retention signal located at the $NH_2$ terminal region of the sialyltransferase are replaced with the cleavable signal peptide of human gamma-interferon. The cleavable signal sequence is required for targeting the modified glycosyltransferase to the secretory machinery of the cell (endoplasmic reticulum, Golgi apparatus, etc.), but the choice of the cleavable sequence is also not particularly critical. Other cleavable sequences could be used such as the insulin signal sequence (47), the tissue plasminogen activator signal sequence (used in the commercial vector pMAMneo-S) or any other cleavable signal sequence. Thus it will be understood that the principles disclosed with respect to the expression and secretion of soluble sialyltransferase (sp-ST) by CHO cells also applies to the other various glycosyltransferases, host cells, vectors and cleavable signal sequences previously mentioned.

The following example demonstrates the production and recovery of a secretable sialyltransferase which is compared to membrane-bound sialyltransferase. The example is as follows:

Materials

The pECE expression vector used to express the membrane-bound sialyltransferase was obtained from Dr. William J. Rutter (University of California at San Francisco School of Medicine-Department of Biochemistry and Biophysics) (23), and CHO cells were obtained from Dr. L. Shapiro (University of California at Los Angeles School of Medicine). Tran $^{35}$S-label (85% methionine and 15% cysteine) (>1000 Ci/mmol) was purchased from ICN Biomedicals, Inc. (Irvine, Calif.), and $\tau$-$^{32}$P-ATP(1000 µCi/ml) was obtained from New England Nuclear (Boston, Mass.). Restriction enzymes used in fusion protein construction were obtained from Bethesda Research Laboratories (Indianapolis, Ind.) and International Biotechnology Incorporated (New Haven, Conn.). All cell culture reagents were obtained from IBCO (Grand Island, N.Y.). Endo-$\beta$-N-acetylglucosaminidase H (Endo H) in 10 mmol/1 phosphate buffer was purchased from Boehringer Mannheim Biochemicals (Indianapolis, Ind.). Immunoprecipititin was obtained from Bethesda Research Laboratories (Gaithersburg, Md.) and prepared according to the manufacturer's directions. Dimethyl sulfoxide was purchased from Sigma (St. Louis, Mo.) and 2.5 diphenyl oxazole was obtained from Aldrich (Milwaukee, Wis.). Methotrexate was purchased from Sigma (St. Louis, Mo.). The expression vector used for expressing the soluble sialyltransferase was PDSVE (described in U.S. patent applications Ser. Nos. 025,344 and 152,045, the contents of which are hereby incorporated by reference).

Construction of the signal peptide-sialyltransferase (sp-ST) fusion protein

To generate a secreted sialyltransferase, the 5' 169 nucleotides (through amino acid 57) of the sialytransferase coding sequence in the ST3 cDNA were replaced with a synthetic gene segment coding for the 23 amino acid signal peptide and first three amino acids of human gamma interferon yielding the fusion gene product shown in FIG. 1. The sialyltransferase coding sequence in the ST3 cDNA was first modified by the introduction of a unique BamH1 site at nucleotides 163–171 (amino acids 55–57) and a unique Sa11 site in the 3' untranslated region at nucleotides 1395–1400 by site-directed mutagenesis (24). The modified BamH-1 Sa11 sialyltransferase gene fragment was isolated and ligated through the BamH1 site, with the synthetic gamma interferon signal peptide gene fragment and inserted into the pDSVE eukaryotic expression vector. Expression of the sialyltransferase gene is driven by the SV40 early gene promoter and uses the SV40 early gene polyadenylation signal. In addition, the vector contains a mouse dihydrofolate reductase (DHFR) gene as a selectable marker (25).

Expression of the membrane-bound and soluble sialyltaransferases in CHO cells

The membrane-bound α2,6 sialyltransferase was expressed via the transfection of CHO DHFR cells with the pECE vector. Isolation of a stably transfected CHO cell clone expressing the membrane-bound a2,6 sialyltransferase from the SV40 early promoter of the pECE vector has been described by Lee et al. (26). The secreted sialyltransferase expression vector was introduced into a CHO DHFR cell line by the calcium phosphate microprecipitation method (27), modified as described (28,29). Following selection by growth in media with dialyzed serum pools of stably transfected CHO cells were obtained, and were further selected with methotraxate stepwise to 0.3 µM.

Pulse-chase analysis and immunoprecipitation of sialyltransferase proteins

CHO cells stably expressing either the wild type sialyltransferase or the sp-ST fusion protein were grown on 100 mm plastic dishes until confluent and then incubated with methionine-free D-MEM for one hour. Media was removed, cells were washed and 2.5 ml methionine-free D-MEM with 100 mCi/ml Trans $^{35}$S-label was added to each dish. After one hour the media was removed, cells were washed with phosphate buffered saline (PBS) and then incubated for various times up to 24 hours with A-MEM, 5% fetal bovine serum (chase period). Following the chase period, media was collected, cells washed in PBS and lysed with 2.5 ml of immunoprecipitation buffer (50 mM Tris-HCl, pH 7.5, 150 mM NaCl, 5 mM EDTA, 0.5% Nonidet P-40, 0.1% SDS).

Sialyltransferase protein was immunoprecipitated from media and cell lysales at each time point. Eight µl of preimmune rabbit serum was incubated with 500 Al of sample for 15 minutex at 25° C. Eighty microliters of a 10% suspension of S. aureus in immunoprecipitation buffer was added to each tube, and incubation was continued for an additional 15 minutes. S. aureus-immune complexes were pelleted by centrifugation at 16,000×g for 1 minute. Supernatants were transferred to a new tube and incubated with 8 µl affinity purified rabbit anti-rat a 2,6 sialyltransferase antibody for approximately 16 hours at 4° C. Again, 80 µl of a 10% suspension of S. aureus was added to each tube and incubation was continued for 30 minutes at 25° C. Samples were always subjected to end-over-end rotation during all of the previously described incubations. S. aureus-immune complexes were pelleted as described above and pellets washed three times with immunoprecipitation buffer and once with 10 mM Tris-HCl, pH 7.5, 0.1% SDS. Sialyltransferase protein was eluted from S. aureus pellets by boiling 5 minutes in 40 µl 1× Laemmli gel sample buffer (10% glycerol, 2% SDS, 65 mM Tris-HCl, pH 7.5, 0.5 mg/ml bromphenol blue, 10% β-mercaptoethanol). Immunoprecipitated proteins were electrophoresed on 10% polyacrylamide gels according to the method of Laemmli (30). Radiolabeled proteins were visualized by fluorography using 2.5 diphenyloxazole/dimethyl sulfoxide (31) and gels were exposed to Kodak XAR-5 film at −80° C.

Endo-β-N-acetylalucosaminidase H diaestions

After the final wash of the S. aureus pellets, immunoprecipitated proteins were treated essentially as described in Dahms et al. (32). Following acetone precipitation, protein pellets were resuspended in 20 µl Endo H buffer (0.1 M sodium citrate, pH 6.0, 0.075% SDS, 0.2% β-mercaptoethanol), 2 mU Endo H was added and the digests were incubated at 37° C. for 16 hours. To stop the digestions, 20 µl of a 2× gel sample buffer was added to each tube and then samples were boiled for 5 minutes in preparation for SDS-polyacrylamide gel electrophoresis.

CDP-hexanolamine-Agarose Affinity Chromatoaraphy

Affinity chromatography of unlabeled and radiolabeled CHO cell media was performed on small columns (1.5 ml) of CDP-hexanolamine-agarose essentially as described by Weinstein et al. (33). Columns were equilibrated with Buffer E (10 mM Na cacodylate, pH 6.5, 0.1% Triton CF-54, 0.15M NaCl) and after application of media (1.25 ml diluted with 1.25 ml of Buffer E) columns were developed by application of 1.2 ml Buffer E, 4.2 ml Buffer H (25 mM Na cacodylate, pH 5.3, 0.1% Triton CF-54, 0.15M NaCl) and 3 ml Buffer H plus 1 mM CDP (Elute, 1 mM CDP). Fractions of 300 µl were collected and assayed for total protein using the Pierce BCA protein detection assay and for sialyltransferase either by direct enzyme activity or by immunoprecipitation of $^{35}$S-labeled sialyltransferase protein followed by SDS polyacrylamide gel electrophoresis.

Sialyltransferase Assay

Sialyltransferase assays were performed essentially as described previously (33) using CMP-[$^{14}$C] NeuAc (285000 cpm/nmole) as a donor substrate and asialo $α_1$ acid glycoprotein (50 µg) as the acceptor substrate. Observed activity in the elution fractions was corrected for the inhibition produced by the presence of CDP in the assay. Activity is reported as cpm transferred/10 µl/hr.

Figure 3:
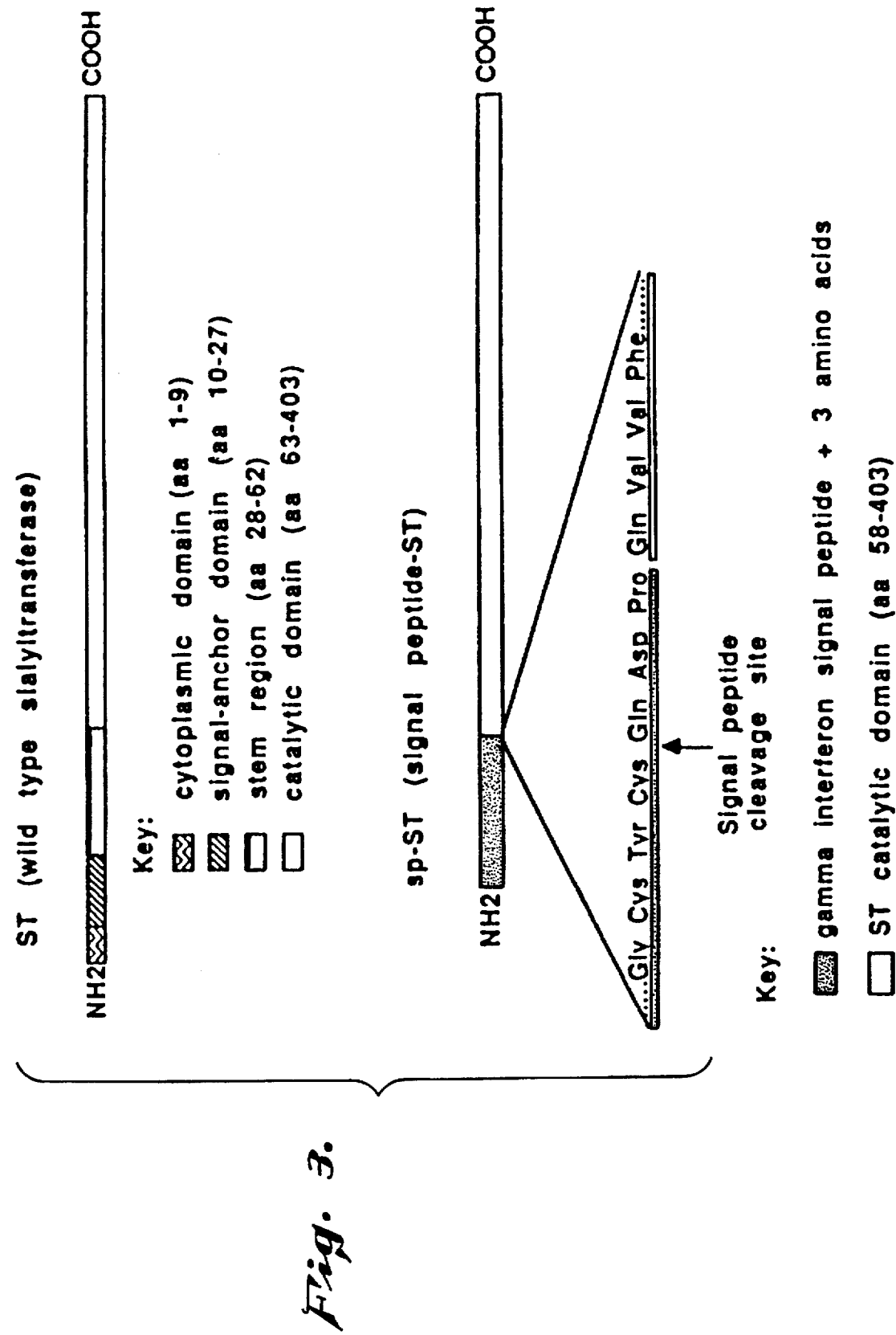
FIG. 3 shows an exemplary construction of a soluble sialyltransferase (sp-ST) in accordance with the present invention as compared to the construction membrane bound sialyltransferase (ST).

In FIG. 3, the structure of the ST (wild type) sialyltransferase is compared to the fusion sialyltransferase (sp-ST). The fusion protein or signal peptide-sialyltransferase (sp-ST), consists of residues 1–26 of human gamma interferon including the cleavable signal peptide (34), and amino acids 58–403 of the sialyltransferase. The NH$_2$-terminal cytoplasmic tail, signal-anchor domain and most of the putative stem region of the wild type sialyltransferase are missing, however, the sp-ST enters the secretory pathway using the gamma interferon signal peptide. CHO cells were transfected with either the wild type sialyltransferase cDNA (26) or the sp-ST cDNA and stably expressing CHO cell clones were isolated as described above.

Figure 4:
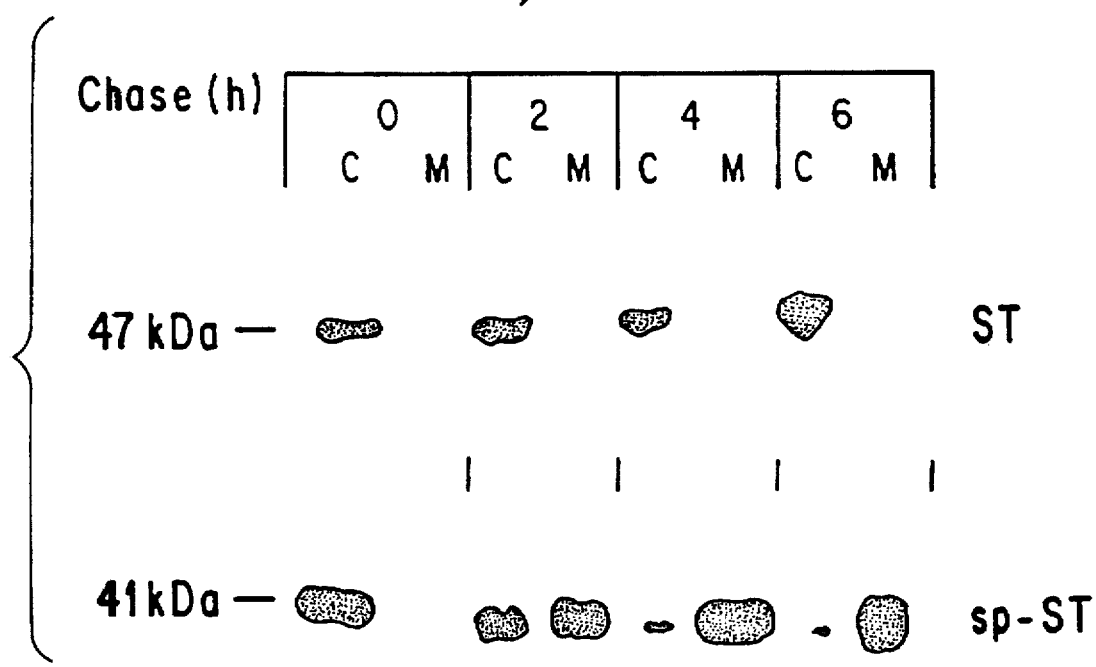
FIG. 4 depicts test results showing secretion of the soluble sialyltransferase (sp-ST) by Chinese hamster ovary (CHO) cells.

The wild type (ST) sialyltransferase (47 kDa) has previously been demonstrated to be catalytically active when expressed in stably transfected CHO cells which are lacking an endogenous β-galactoside α2,6 sialyltransferase (26). The above described pulse-chase analysis and immunoprecipitation of sialyltransferase protein from cell lysates and media of CHO cells revealed that the wild type sialyltransferase remains cell associated for up to 6 hours of chase and is not detected in the media for up to 24 hours (see FIG. 4). In contrast to the wild type sialyltransferase, the sp-ST fusion protein construct is rapidly secreted from CHO cells. At least 50% of the total sp-ST protein is secreted within 2 hours of chase, following a 1 hour labeling period (see FIG. 4). Moreover, the apparent molecular weight of the sp-ST (41 kDa) is consistent with the cleavage of the 2.5 kDa gamma interferon signal peptide.

Figure 5:
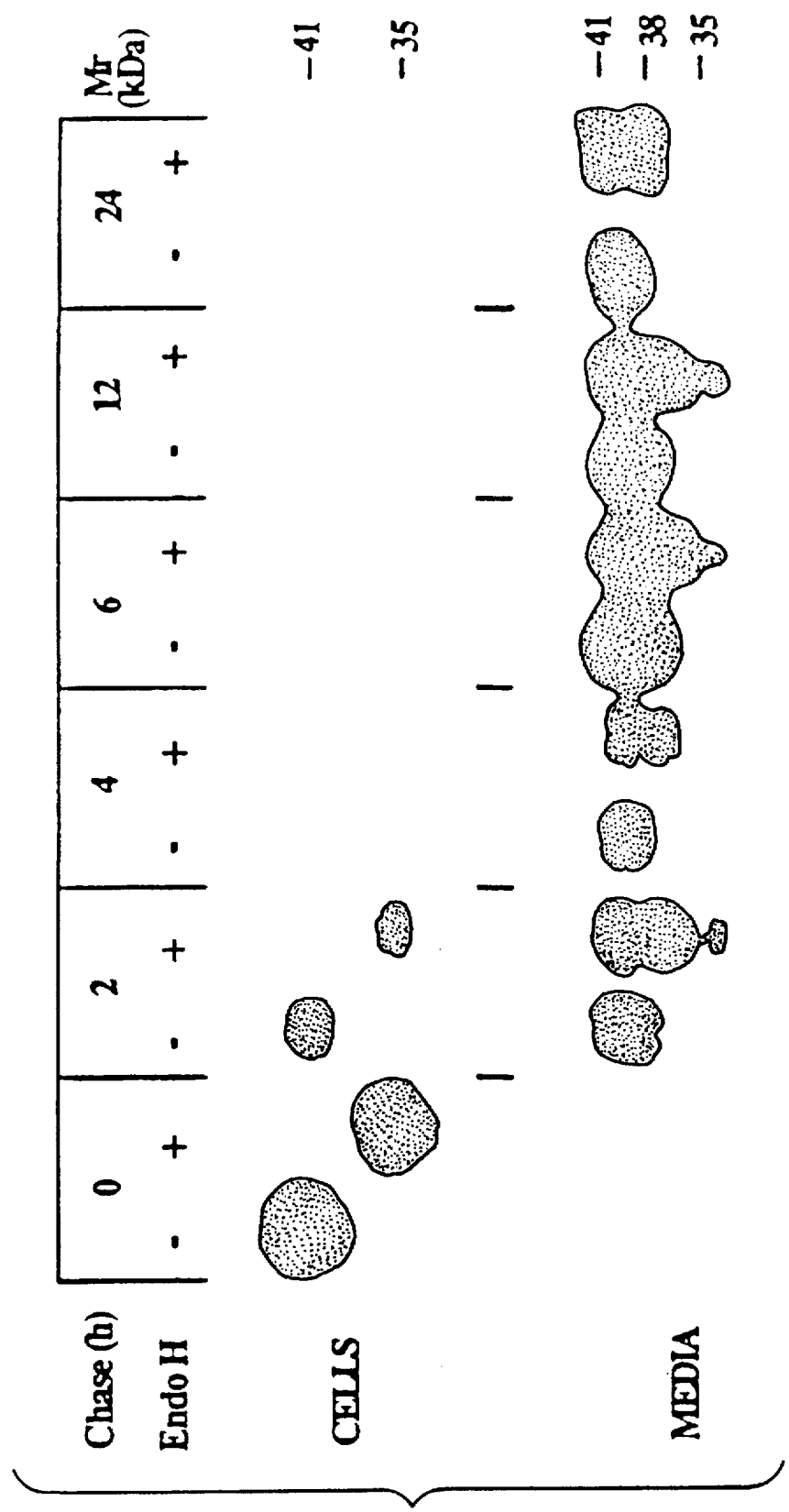
FIG. 5 shows test results demonstrating that the intracellular form of ST is sensitive to Endo H while the secreted ST is resistant to Endo H.

Endo-β-N acetylglucosaminidase H (Endo H) preferentially cleaves high mannose N-linked oligosaccharides and can be used to trace the movement of secretory proteins from the ER to medial-Golgi apparatus where processing reactions convert the sugar chains to Endo H resistant forms (2,35). Endo H sensitivity of the N-linked oligosaccharides of both the intracellular and secreted forms of the sp-ST, which contains two N-linked sugar chains, is shown in FIG. 5. The intracellular form of the sp-ST protein (41 kDa) is predominantly Endo H sensitive and yields a single band with an apparent molecular weight of 35 KDa consistent with the cleavage or both N-linked carbohydrate groups. In contrast, the secreted sp-ST fusion protein is largely resistant to Endo H yielding 38 kDa and 41 kDa bands, indicating the resistance of one or both N-linked carbohydrate groups to enzyme digestion, respectively. Because these resistant forms of the sp-ST do not accumulate intracellularly, the results suggest that the rate limiting step in the secretion of the sp-ST is in the protein's migration from ER to the Golgi apparatus. Once the sp-ST oligosaccharides are processed in the Golgi apparatus, the sp-ST protein is rapidly secreted.

Figure 6:
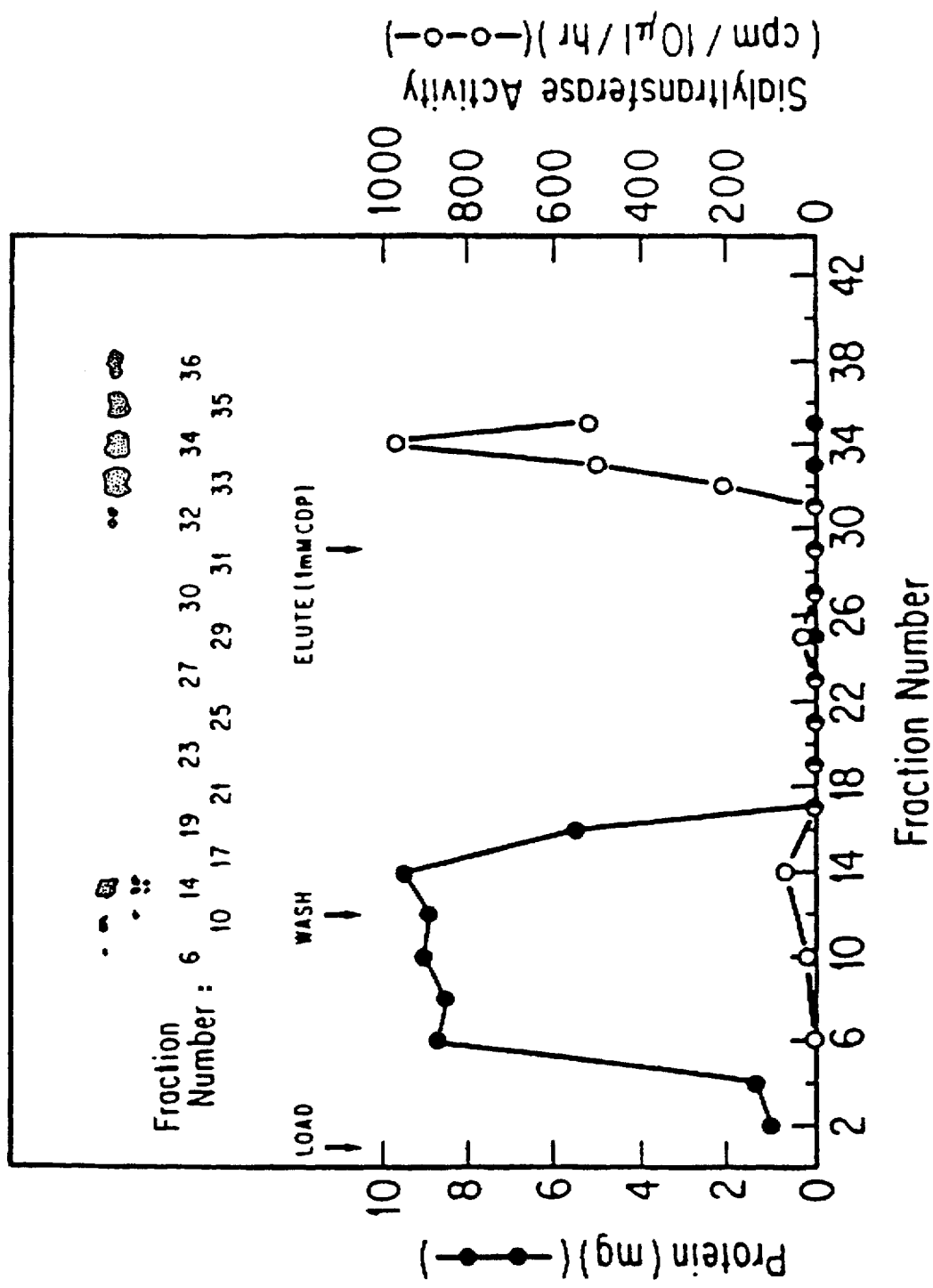
FIG. 6 depicts test results showing that the soluble sp-ST retains sialyltransferase activity.

As with the wild type sialyltransferase, the CHO cells expressing the sp-ST synthesize the product of the enzyme detected by the FITC-SNA lectin which shows that the soluble sialyltransferase exhibits catalytic activity during transit through the cell. Moreover, direct enzyme assays detected sialyltransferase activity in the media of CHO cells secreting the sp-ST protein, but not in the media of parental CHO cells or CHO cells expressing the wild type sialyltransferase. This shows that the soluble enzyme is active once secreted from the cells. The ability of sp-ST to bind to the affinity absorbent CDP-hexanolamine-agarose used in the purification of the rat liver sialyltransferase was tested (33). As demonstrated in FIG. 6, sialyltransferase activity in the CHO cell media is bound to the column and elutes with the free ligand CDP. Moreover, the bulk of the immunoprecipitable $^{35}$S-labeled sp-ST accumulated throughout a 24 hour chase period is also bound to the column and is specifically eluted with CDP. Taken together, these results demonstrate that the secreted enzyme is catalytically active and is stable in the media.

Figure 2:
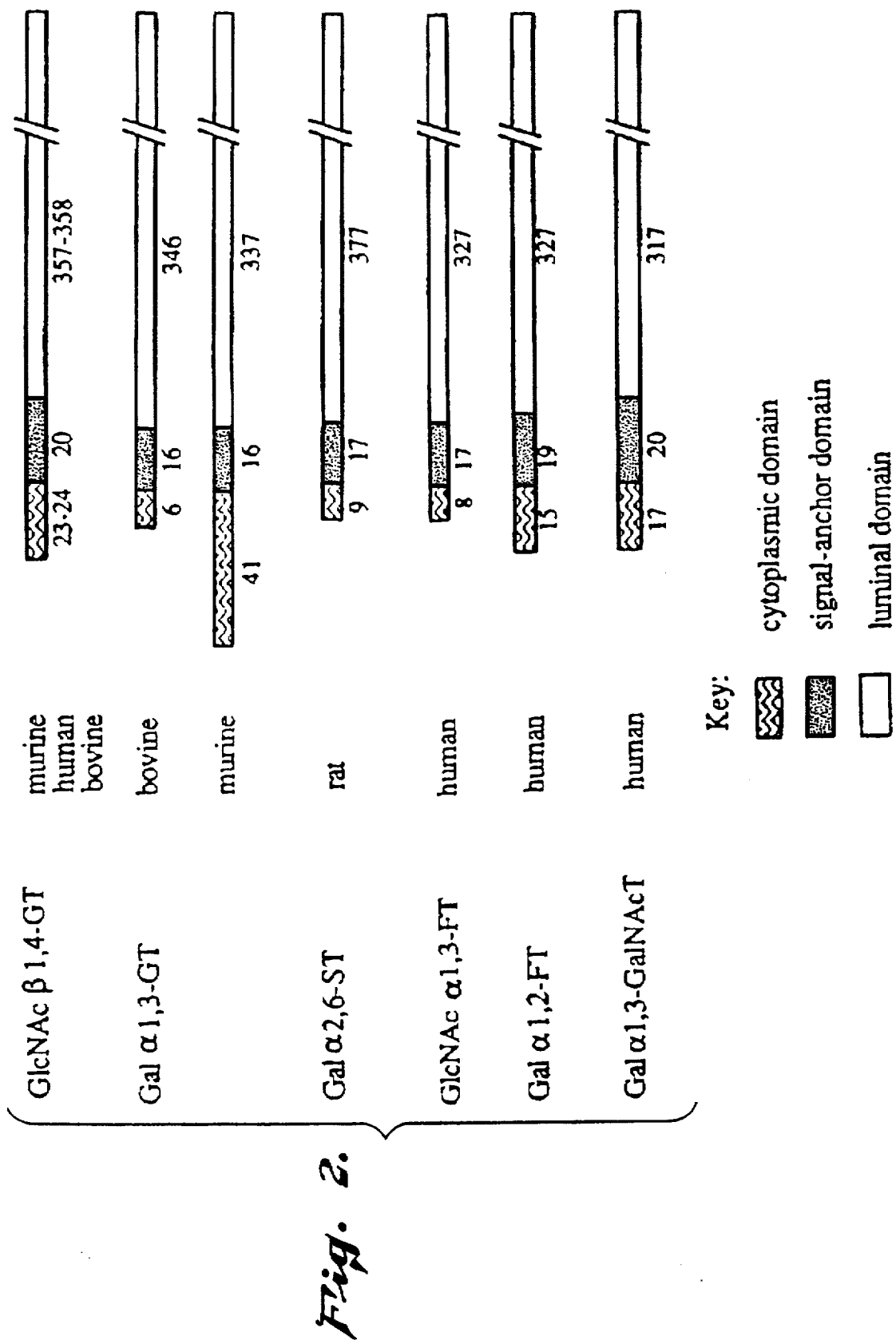
FIG. 2 compares the essential features of cloned cDNA's to other Golgi apparatus glycosyltransferases, all of which contain $NH_2$-terminal hydrophobic membrane domains, predicting each to have the same topology as the sialyltransferase (44).

The same principles illustrated in the above example can be extended to the production of any Golgi apparatus glycosyltransferase or other processing enzyme (glycosidase, sulfotransferase, acetyltransferase etc.) as a secretory protein providing that the enzyme has an $NH_2$-terminal signal-anchor sequence and has the Golgi retention signal in the $NH_2$-terminal peptide sequence including the cytoplasmic tail, membrane anchor and stem regions which are not required for catalytic activity. All Golgi apparatus glycosyltransferases whose cDNAs have been cloned meet this criterion (FIG. 2 and Table 1). In addition, a Golgi glycosidase, mannosidase II, has also been shown to have a similar domain structure to the exemplary sialyltransferase illustrated in FIG. 1 (48).

All publications and patent applications referred to above and in the bibliography below are incorporated herein by reference to the same extent as if each individual reference was specifically and individually incorporated herein by reference. Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiment illustrated herein, but is only limited by the following claims.

BIBLIOGRAPHY

1. Pfeffer, S. and Rothman, J. E. (1987) Annu. Rev. Biochem. 56, 829–852.

2. Wieland, F. T., Gleason, M. L., Serafini, T. A., and Rothman, J. E. (1987) Cell 50, 289–300.

3. Klausner, R. D. (1989) Cell 57, 703–706.

4. von Figura, K. and Hasilik, A. (1986) Annu. Rev. Biochem. 55, 167–193.

5. Kornfeld, S. (1986) J. Clin. Invst. 77, 1–6.

6. Munro, S. and Pelham, H. R. B. (1987) Cell 48, 899–907.

7. Pelham, H. R. B. (1988) EMBO J. 7, 913–918.

8. Paabo, S., Bhat, B. M., Wold, W. S. M., and Peterson, P. A. (1987) Cell 50, 311–317.

9. Poruchynsky, M. S. and Atkinson, P. H. (1988) J. Cell Biol. 107, 1697–1706.

10. Stirzaker, S. C. and Both, G. W. (1989) Cell 56, 741–747.

11. Machamer, C. E. and Rose, J. K. (1987) J. Cell Biol. 105, 1205–1214.

12. Fleischer, B. (1981) J. Biol. Chem. 89, 246–255.

13. Kornfeld, R. and Kornfeld, S. (1985) Annu. Rev. Biochem. 54, 631–664.

14. Roth, J., Taatjes, D. J., Lucoq, J. M., Weinstein, J., and Paulson, J. C. (1985) Cell 43, 287–295.

15. Roth, J., Taatjes, D. J., Weinstein, J., Paulson, J. C., Greenwell, P., and Watkins, W. M. (1986) J. Biol. Chem. 261, 14307–14312.

16. Taatjes, D. J., Roth, Weinstein, J., and Paulson J. C. (1988) J. Biol. Chem. 263, 6302–6309.

17. Weinstein, J., Lee, E. U., McEntee, K., Lai, P. H., and Paulson, J. C. (1987) J. Biol. Chem. 263, 17735–17743.

18. Paulson, J. C., Beranek, W. E., and Hill, R. L. (1977) J. Biol. Chem. 252, 2356–2362.

19. Hudgin, R. L. and Schachter, H. (1971) Can. J. Biochem. 49, 829–837.

20. Kaplan, H. A., Woloski, B. M. R. N. J., Hellman, M., and Jamieson, J. C. (1985) J. Biol. Chem. 258, 11505–11509.

21. Lammers, G. and Jamieson, J. C. (1988) Biochem. J. 256, 623–631.

22. Paulson, J. C. Weinstein, J., Ujita, E. L., Riggs, K. J., and Lai, P. H. (1987) Biochem. Soc. Trans. 15, 618–620.

23. Ellis, L., Clauser, E., Morgan, D. O., Edery, M., Roth, R. A., and Rutter, W. A. (1986) Cell 45, 721–732.

24. Zoller, J. J. and Smith, M. (1983) Meth. Enzymol. 100, 468–500.

25. Gasser, C. S., Simonsen, C. C., Schilling, J. W., and Schimke, R. T. (1982) Proc. Natl. Acad. Sci. USA 79, 6522–6526.

26. Lee, E. U., Roth, J., and Paulson, J. C. (1989) J. Biol. Chem., in press.

27. Graham, F. L. and van der Eb, A. J. (1973) Virology, 52, 456–467.

28. Wigler, M., Pellicer, A., Silverstein, S., and Axel, R. (1978) Cell 41, 725–731.

29. Lewis, W. H., Srinivasan, P. R., Siokoc, N., and Siminovitch, L. (1980) Somatic Cell Genetics 6, 333–347.

30. Laemmli, U. K. (1970) Nature 227, 680–685.

31. Bonner, W. M. and Lasky, R. A. (1974) Eur. J. Biochem. 46, 83–88.

32. Dahms, N. M., Lobel, P., Breitmeyer, J., Chirgwin, J. M., and Kornfeld, S. (1987) Cell 50, 181–192.

33. Weinstein, J. de Souza-e-Silva, U., and Paulson, J. C. (1982) J. Biol. Chem. 257, 13835–13844.

34. Gray, P. and Goeddel, D. V. (1982) Nature 298, 859–863.

35. Maley, F. and Trimle, R. B. (1981) J. Biol. Chem. 256, 1088–1090.

36. Roth, J. and Berger, E. G. (1982) J. Cell Biol. 93, 223–229.

37. Shaper, N. L., Hollis, G. F., Douglas, J. G., Kirsch, I. R., and Shaper, J. H. (1988) J. Biol. Chem. 263, 10420–10428.

38. Nakazawa, K., Ando, T., Kimura, T., and Narimatsu, H. (1988) J. Biochem. (Tokyo) 104, 165–168.

39. Masri, K. A., Appert, H. E., and Fukuda, M. N. (1988) Biochem. Biophys. Res. Comm. 157, 657–663.

40. Berger, E. G. and Hesford, F. J. (1985) Proc. Natl. Acad. Sci. USA 82, 4736–4739.

41. Duncan, J. R. and Kornfeld, S. (1988) J. Cell Biol. 106, 617–628.

42. Beyer, T. A., Sadler, J. E., Rearick, J. I., Paulson, J. C., and Hill, R. L. (1981) Adv.Enzymol. 52, 23–175.

43. Toone, E. J., Simon, Es., Bednarski, M. D., and Whitesides, G. M. (1989) Tetrahed. Rep., in press.

44. Colley, K. M., Lee, E. U., Adler, B., Browne, J. K. and Paulson, J. C. (1989) J. Biol. Chem. 264, in press.

45. Ash, J. F., Fineman, R. M., Kalka, T., Morgan, M. and Wire, B. (1984) J. Cell Biol. 99, 971–983.

46. Smith, G. E., Summers, M. D. and Fraser, M. J. (1983) Mol. Cell Biol. 3, 2156–2165.

47. Hsueh, E. C., Holland, E. C., Carrera, G. M., and Drickamer, K. (1986) J. Biol. Chem. 261, 4940–4947.

48. Moreman, K. W. (1989) Proc. Nat. Acad. Sci. USA 85, 5276–5280.

---

What is claimed is:

1. An expression cassette comprising a promoter operably linked to a DNA sequence, said DNA sequence encoding a secretable glycosyltransferase which lacks the membrane anchor and golgi retention signal.

2. An expression cassette according to claim 1 wherein the DNA sequence is a cDNA sequence.

3. An expression cassette according to claim 1 wherein the DNA sequence encodes a glycosyltransferase which consists of a catalytic domain and less than ten stem region amino acid residues.

4. An expression cassette according to claim 1 further comprising a DNA sequence encoding a cleavable signal sequence in operable linkage to said DNA sequence encoding said secretable glycosyltransferase.

5. An expression cassette according to claim 4 wherein said DNA sequence encoding the cleavable signal sequence encodes a human γ-interferon signal sequence.

* * * * *